US010481136B2

(12) United States Patent
Stearns et al.

(10) Patent No.: US 10,481,136 B2
(45) Date of Patent: Nov. 19, 2019

(54) CHROMATOGRAPHIC SYSTEM TEMPERATURE CONTROL SYSTEM

(71) Applicant: Valco Instruments Company, L.P., Houston, TX (US)

(72) Inventors: Stanley D. Stearns, Houston, TX (US); Huamin Cai, Houston, TX (US); Chris Bishop, Houston, TX (US); Robert Simpson, Houston, TX (US); Chris S. Cowles, Houston, TX (US); Dale Ashworth, Houston, TX (US); Douglas Dailey, Houston, TX (US)

(73) Assignee: Valco Instruments Company, L.P., Houston, TX (US)

(*) Notice: Subject to any disclaimer, the term of this patent is extended or adjusted under 35 U.S.C. 154(b) by 0 days.

(21) Appl. No.: 16/411,397

(22) Filed: May 14, 2019

(65) Prior Publication Data

US 2019/0265209 A1 Aug. 29, 2019

Related U.S. Application Data

(62) Division of application No. 15/441,372, filed on Feb. 24, 2017, now Pat. No. 10,324,069.

(51) Int. Cl.
*G01N 30/30* (2006.01)

(52) U.S. Cl.
CPC ..... *G01N 30/30* (2013.01); *G01N 2030/3069* (2013.01); *G01N 2030/3084* (2013.01)

(58) Field of Classification Search
None
See application file for complete search history.

(56) References Cited

U.S. PATENT DOCUMENTS

| 4,923,486 | A | * | 5/1990 | Rubey ............... G01N 30/30 95/87 |
| 5,028,243 | A | * | 7/1991 | Rubey ............... G01N 30/30 95/87 |
| 5,028,246 | A | | 7/1991 | Sarkar |
| 5,105,067 | A | | 4/1992 | Brekkenstran et al. |
| 5,553,622 | A | | 9/1996 | McKown et al. |
| 5,755,670 | A | | 5/1998 | McKown et al. |
| 5,793,022 | A | | 9/1998 | Klinck |

(Continued)

FOREIGN PATENT DOCUMENTS

| CN | 1930917 A | 3/2007 |
| EP | 1262649 B1 | 4/2002 |

(Continued)

OTHER PUBLICATIONS

Mark H. Paschall, International Search Report (PCT/US07/63861), dated Aug. 7, 2008, 2 pages, United States Patent and Trademark Office as International Search Authority, Alexandria, Virginia US.

(Continued)

*Primary Examiner* — Paul M. West
*Assistant Examiner* — Mark A Shabman
(74) *Attorney, Agent, or Firm* — Crain, Caton & James, P.C.; James E. Hudson, III

(57) ABSTRACT

A temperature controller for simultaneously controlling the temperatures of a plurality of heating elements for use in chromatographic analysis including columns, detectors, valves, transport lines and other components.

1 Claim, 5 Drawing Sheets

(56) References Cited

U.S. PATENT DOCUMENTS

| | | | |
|---|---|---|---|
| 5,808,178 A * | 9/1998 | Rounbehler | G01N 30/30 |
| | | | 73/23.35 |
| 6,252,209 B1 | 6/2001 | Liepold | |
| 6,519,546 B1 | 2/2003 | Eryurek et al. | |
| 6,579,345 B2 | 6/2003 | Munari | |
| 7,193,187 B2 | 3/2007 | Chen | |
| 7,442,902 B2 | 10/2008 | Stearns et al. | |
| 8,642,931 B2 | 2/2014 | Stearns et al. | |
| 8,772,680 B2 | 7/2014 | Stearns et al. | |
| 8,890,039 B2 | 11/2014 | Etscheid et al. | |
| 9,134,180 B2 | 9/2015 | James et al. | |
| 9,570,415 B2 | 2/2017 | Park et al. | |
| 9,927,406 B1 * | 3/2018 | Pierce | G01N 30/30 |
| 2002/0178912 A1 * | 12/2002 | Munari | G01N 30/30 |
| | | | 95/87 |
| 2004/0056753 A1 | 3/2004 | Chiang et al. | |
| 2005/0205549 A1 | 9/2005 | Crawford et al. | |
| 2005/0268693 A1 * | 12/2005 | Hasselbrink | G01N 30/465 |
| | | | 73/23.42 |
| 2006/0144126 A1 * | 7/2006 | O'Brien | G01N 1/2202 |
| | | | 73/23.42 |
| 2007/0210285 A1 | 9/2007 | Stearns et al. | |
| 2009/0045187 A1 | 2/2009 | Stearns et al. | |

FOREIGN PATENT DOCUMENTS

| | | |
|---|---|---|
| WO | 199100131 A1 | 1/1991 |
| WO | 2007106803 A2 | 9/2007 |

OTHER PUBLICATIONS

Mark H. Paschall, Written Opinion (PCT/US07/63861), dated Aug. 7, 2008, 4 pages, United States Patent and Trademark Office as International Search Authority, Alexandria, Virginia US.

Lee W. Young, Written Opinion of the International Search Authority (PCT/US09/56963), dated Oct. 22, 2009, 5 pages, United States Patent and Trademark Office as Search Authority, Alexandria, Virginia, US.

Lee W. Young, International Search Report (PCT/US09/56963), dated Oct. 22, 2009, 2 pages, United States Patent and Trademark Office as Search Authority, Alexandria, Virginia, US.

Ken Wieder, International Preliminary Report on Patentability (PCT/US09/56963), dated Jan. 11, 2011, 7 pages, United States Patent and Trademark Office as Search Authority, Alexandria, Virginia, US.

Ken Wieder, Notification of Transmittal of International Preliminary Report on Patentability (PCT/US09/56963), dated Jan. 11, 2011, 2 pages, United States Patent and Trademark Office as Search Authority, Alexandria, Virginia, US.

Lars Theunissen, Summons to attend oral proceeding pursuant to Rule 115(1) EPC (EPO Application 07758413.4), dated Oct. 27, 2011, 7 pages, European Patent Office, Munich, Germany.

Zhenwen-Wang, Accurate modeling of thin film resistor up to 40 GHz, ESSDERC 2002: 32nd European Solid-State Device Research Conference, Sep. 24-26, 2002, 4 pages (pp. 307-310), Firenze, ISBN 88-900847-8-2.

D. H. Galvan Effect of Silver in Y1Ba2Cu3O7-x samples, Journal of Materials Science, vol. 29, No. 10, 1994, 6 pages (pp. 2713-2718), Heidelberg, Allemagne, ISSN: 0022-2461.

Lars Theunissen, Communication pursuant to Article 94(3) EPC (EPO Application 07758413.4), dated Aug. 10, 2011, 4 pages, European Patent Office, Munich, Germany.

Phillipe Mallet Communication pursuant to Article 94(3) EPC (EPO Application 07758413.4), dated Dec. 15, 2010, 4 pages, European Patent Office, Munich, Germany.

First Office Action dated Jan. 7, 2011—Chinese Patent Application 2007800088773, Jan. 17, 2011, 3 pages, State Intellectual Property Office, People's Republic of China, Beijing, China.

Uta Muller, Supplementary European Search Report (EP 09 822 380.3), dated Mar. 2, 2012, 9 pages, European Patent Office, Munich, Germany.

Uta Muller, European Patent Office Examination Report—EP 09 822 380.3-2206, dated Aug. 29, 2012, 6 pages, European Patent Office, Munich, Germany.

Graime Evans, IP Australia Patent Examination Report No. 1-2009 307982, Apr. 9, 2013, 3 pages, IP Australia, Government of Australia, Woden, ACT, Australia.

Jack Redfern, Response to IP Australian Patent Examination Report No. 1-2009 307982, 48 pages, ShelstonIP, Syndey, NSW, Australia.

IP Australia Notice of Acceptance—2009 307982, dated Jun. 7, 2013, 2 pages, IP Australia, Government of Australia, Woden, ACT, Australia.

Abdulmalik Lawal, Response to EP Office Examination Report—EP 09 822 380.3-2206, dated Nov. 5, 2012, 16 pages, Murgitroyd & Co., Ltd., Glasgow, UK.

First Office Action—China Patent Application 200980152498.0, dated Dec. 4, 2012, 5 pages (7 page translation), State Intellectual Property Office, Peoples Republic of China, Haidan District, Beijing, China.

Mark H. Paschall, International Preliminary Examination Report—PCT/US07/63861, dated Feb. 26, 2009, 3 pages, United States Patent and Trademark Office as International Search Authority, Alexandria, Virginia US.

Second Office Action—CN2009801524498.0, dated Jul. 15, 2013, 5 pages, State Intellectual Property Office, People's Republic of China, Beijing, China.

Taku Kakizaki, Reasons for rejection—JP2011-533205, dated Oct. 3, 2013, 2 pages, Japanese Patent Office, Tokyo, Japan.

Blaine R. Copenheaver, Notification of Transmittal of the International Search Report and the Written Opinion of the International Search Authority, or the Declaration, International Search Report , Written Opinion of the International Searching Authority—PCT/US2018/019695, dated May 16, 2018, 13 pages, United States Patent & Trademark Office as the International Searching Authority, Alexandria, Virginia.

Nimesh Patel, Notification of Transmittal of International Preliminary Report on Patentability and the International Preliminary Report on Patentability—PCT/US18/19695, dated Apr. 26, 2019, 5 pages, United States Patent and Trademark Office as the International Preliminary Examination Authority, Alexandria, Virginia, USA.

* cited by examiner

CHROMATOGRAPHIC SYSTEM TEMPERATURE CONTROL SYSTEM

CROSS REFERENCE TO RELATED APPLICATIONS

This application is a divisional of U.S. patent application Ser. No. 15/441,372 for "Chromatographic System Temperature Control System" filed Feb. 24, 2017, which is incorporated by reference, the benefit of priority to which is hereby claimed.

STATEMENT REGARDING FEDERALLY SPONSORED RESEARCH OR DEVELOPMENT

Not Applicable.

BACKGROUND OF THE INVENTION

1. Field of the Invention

This invention pertains to a temperature controller for simultaneously controlling the temperatures of a plurality of heating elements for use in chromatographic analysis including columns, detectors, valves, transport lines and other components. In particular, the device controls the temperature of a heating element associated with each component, monitors the temperature of each component and replicates the temperature profile of the first component at the remaining components. The device thus pertains to controlling the temperature of a plurality of heating elements for use in chromatographic analysis including columns, detectors, valves, transport lines and other components, although it may be used in any system wherein precise heating through a range of temperatures is desired.

2. Description of the Related Art

An adaptive temperature controller for use with any electrically-conductive material is disclosed. In chromatographic analysis, the chromatographic column is heated according to a temperature profile, which may profile multiple temperature settings at various times during operation. Temperature is known to substantially alter the effectiveness of the column, affecting efficiency and repeatability of the separation. The columns are associated with necessary related equipment, such as the sample injector, valves, transport lines, and detectors. As maintaining temperature of the sample and the resulting separation is of importance, it is known in the art to position the column in an oven and to position the remaining components in the oven or abutting its external walls. These column ovens, however, tend to be substantial in volume, consuming substantial space, and heavy, precluding transport. Alternatively, the balance of the components may be positioned in a static air bath, encapsulated in their own air baths, resulting in the consumption of substantial volumes of laboratory space. Thus, it is often necessary to maintain portions of test equipment or other items above ambient temperature. This has been accomplished in the prior art with various temperature controllers and heating apparatus. It is well known to provide a source of heat that is easily controlled. Most often heat is transferred from a conductive element. In the prior art, the temperature of such conductive element was monitored by a separate device, often a Resistance Temperature Detector (RTD). However, this requires multiple parts, further increasing the space consumed by such equipment, and also increasing the weight of such equipment, and its cost. Additionally, such systems often were unable to produce rapid temperature changes and were unable to replicate across the associated chromatographic components the temperature change applied to the column. Moreover, heating and cooling of a particular piece of equipment was not uniform and often was not sufficiently fast, requiring delay in testing until the equipment reached the desired temperature by heating or cooling. This shortcoming has been evidence in systems based about gas chromatograph ovens, wherein the chromatographic column is maintained at temperature within an oven. While the oven provided a bath of air heated to a temperature, the samples generally entered the column from a transport line at room temperature, generating a cold spot.

It would therefore be a desirable improvement to have a temperature controller with fewer parts that likely would reduce weight, space and cost, would provide and ensure near-uniform heating of the associated components, and could be capable of rapid heating and cooling.

SUMMARY

The adaptive temperature controller disclosed herein includes a device for measuring electrical resistance, an electrically-conductive material, and a power supply. In operation, the controller determines the resistance of the electrically-conductive material at one or more predetermined temperatures and is able to determine the corresponding resistance of the electrically-conductive material at other temperatures within a temperature range and to apply the voltage or current necessary to obtain such resistances. The predetermined (calibration) temperatures of the electrically-conductive material may be determined by using a temperature sensor or by approximation based on ambient air temperature. As a result, the voltage or power may be instantly varied to produce near infinite control over material temperature.

The foregoing and other objectives, features, and advantages of the disclosure will be more readily understood upon consideration of the following detailed description of the disclosure, taken in conjunction with the accompanying drawings.

BRIEF DESCRIPTION OF THE DRAWINGS

So that the manner in which the described features, advantages and objects of the disclosure, as well as others which will become apparent, are attained and can be understood in detail, a more particular description of the disclosure briefly summarized above may be had by reference to the embodiments thereof that are illustrated in the drawings, which drawings form a part of this specification. It is to be noted, however, that the appended drawings illustrate only typical preferred embodiments of the disclosure and are therefore not to be considered limiting of its scope as the disclosure may admit to other equally effective embodiments.

DETAILED DESCRIPTION OF THE PREFERRED EMBODIMENT

Figure 1A:
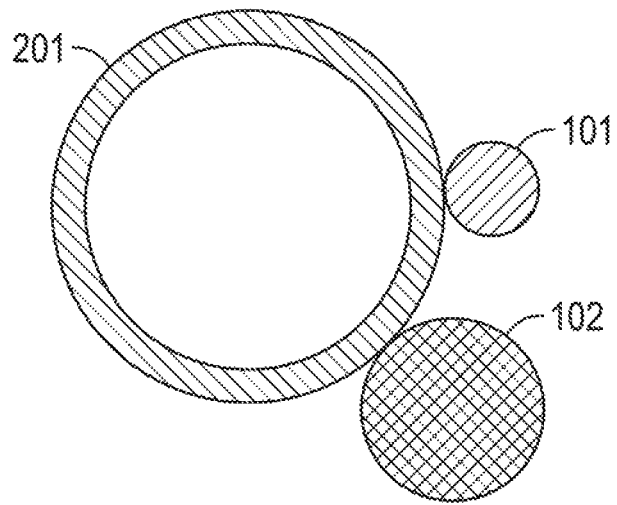
FIG. 1a depicts a cross-sectional view of one embodiment of the prior art.
Figure 1B:
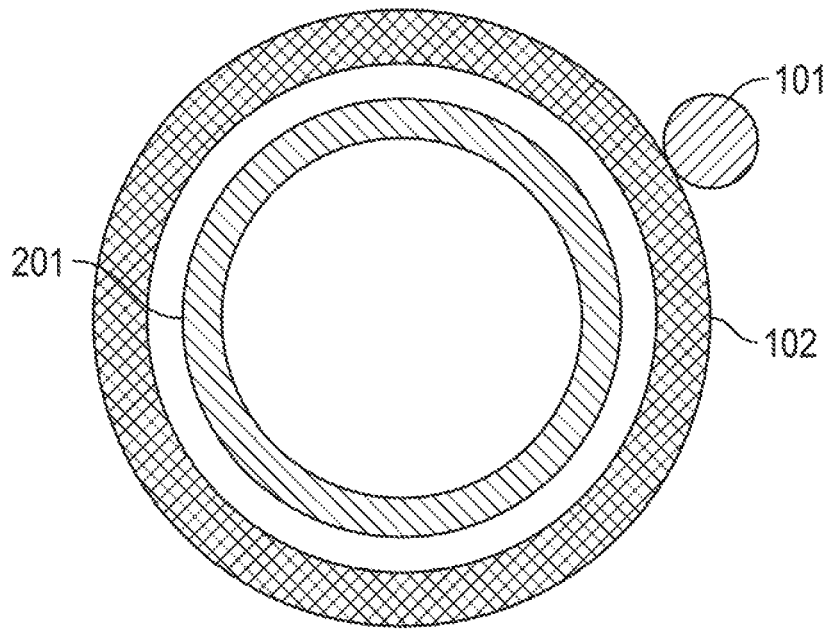
FIG. 1b depicts a cross-sectional view of another embodiment of the prior art.

As depicted in FIGS. 1a and 1b, temperature controllers are known where a conductive element 102 and a sensor 101 were placed in proximity to or about one component 201 of a system 200 to respectively heat and monitor the temperature of that single component 201. It is well known to provide a source of heat that is easily controlled. Most often heat is transferred from a conductive element 102 to be subsequently distributed to component 201. The conductive element 102 may be placed adjacent (FIG. 1a) or surrounding (FIG. 1b) element 301.

Figure 2:
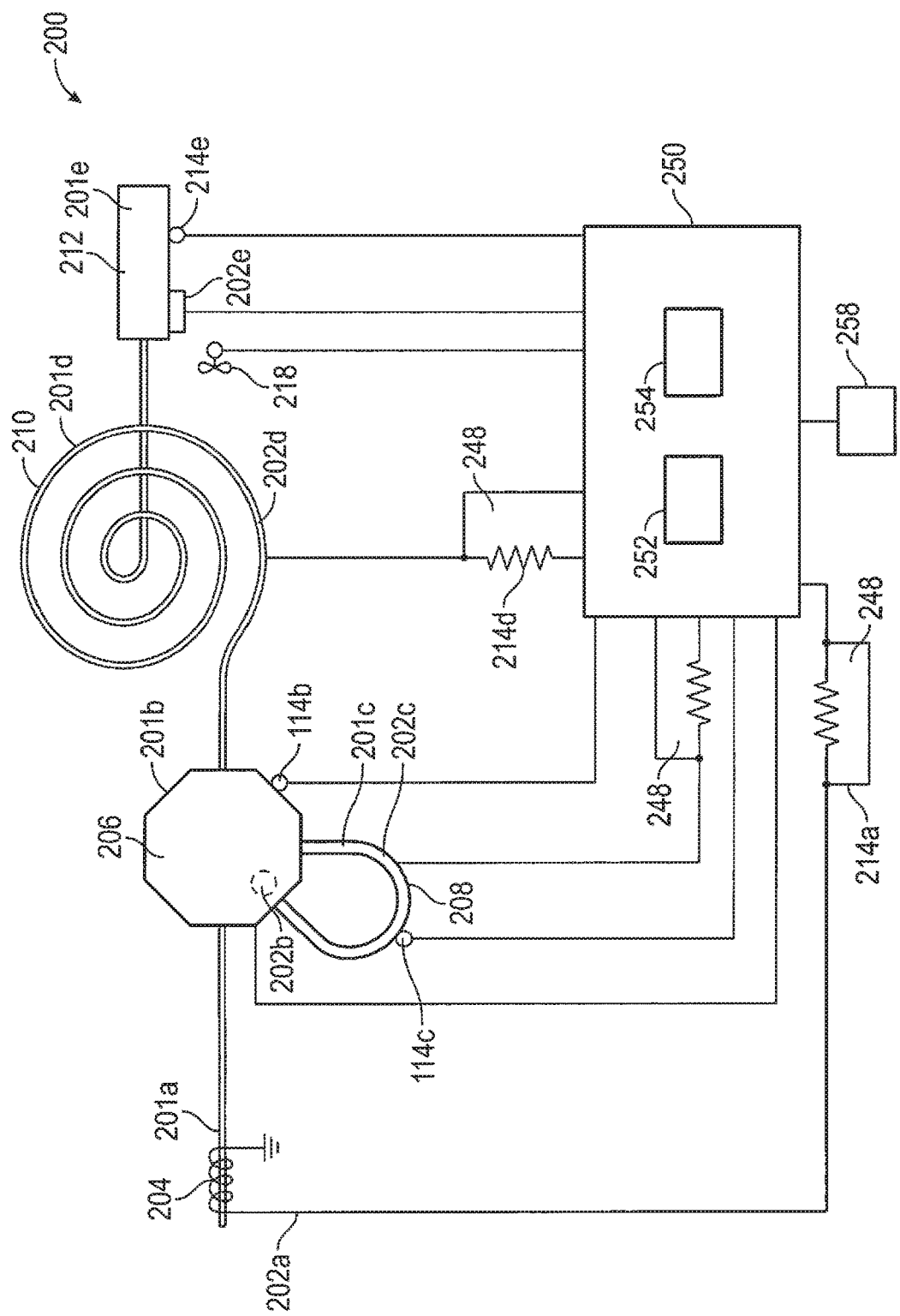
FIG. 2 illustrates one embodiment of the present disclosure.

Referring to FIG. 2, the chromatographic system 200 may include a plurality of components 201a, 201b, 201c, 201d, 201e, such as transfer lines 204, injection valves 206, sample loops 208, columns 210 and detectors 212. In some situations, a valve 206 may be connected to the output of the sample loop 208 and the input of the column 210. The column 210 may be a coiled bundle. In other chromatographic systems 200, a valve 206 may be connected to the input and output of the sample loop 208 and the column 210 and to the input of a detector 212. In other chromatographic systems 200, the valve may also be connected to the output from the detector 212. In a chromatographic system 200, multiple valves 206 may be positioned intermediate the components 204, 206, 208, 210, and 212. In each chromatographic system 200, it may be necessary alter temperature, by heating or permitting cooling, each of those components 204, 206, 208, 210, and 212 to maintain a common temperature profile for the test duration. This requires chromatographic system 200 to control heating of each, or all, of the components 204, 206, 208, 210, and 212, potentially increasing the space consumed by such equipment, the weight of such equipment, and its cost. The present disclosure provides for common control of heating of the various components by a single temperature controller 250.

Referring to FIG. 2, a heating element 202a, 202b, 202c, 202d, and 202e, which may be an electrically-conductive material, is used to alter the temperature, by heating or permitting cooling, of each of the components 204, 206, 208, 210 and 212 of a chromatography system 200, directly or indirectly.

In direct heating, the heating element is the component 201a, 201b, 201c, 201d, 201e itself, composed, at least in part, or jacketed by electrically-conductive material 114. Direct heating may thus be most effective for a component 201a, 201b, 201c, 201d, 201e such as a transport line 204 or a column 210. In indirect heating, the component 201a, 201b, 201c, 201d, 201e is contacted by a separate heating element 202a, 202b, 202c, 202d, and 202e. Indirect heating therefore may be most effective for components 201a, 201b, 201c, 201d, 201e wherein the component body is not sufficiently electrically conductive, such as a valve 206, or where electrical interference is undesirable, such as in a detector 212. A bundled column 210, for example, may include within the bundle one or more nickel wires. Regardless of the type of heating used, the temperature of the component 201a, 201b, 201c, 201d, 201e, the rate of heating, and the duration of heating at any temperatures, are controlled by temperature controller 250. As illustrated in FIG. 2, the system 200 may include a combination of direct and indirect heating.

In direct heating, the heating element 202a, 202b, 202c, 202d, and 202e used in conjunction with temperature controller 250 has a known electrical resistance as a function of temperature. The temperature controller 250 is in electrically-conductive communication with the heating element 202a, 202b, 202c, 202d, and 202e. The relationship between resistance and temperature for the heating element 202a, 202b, 202c, 202d, and 202e may be obtained by the temperature controller 250 by application of an equation or by interpolation from a table of such data. Such heating element 202a, 202b, 202c, 202d, and 202e is therefore in close contact with the component 201a, 201b, 201c, 201d, 201e. Since the electrical resistance of a heating element 202a, 202b, 202c, 202d, and 202e is known as a function of temperature, the temperature of the heating element 202a, 202b, 202c, 202d, and 202e can be determined by a dynamic measurement of the electrical resistance of the heating element 202a, 202b, 202c, 202d, and 202e. The temperature of the components 204, 206, 208, 210 and 212 may therefore be controlled by the current (or voltage or both) applied to the heating element 202a, 202b, 202c, 202d, and 202e. In the preferred embodiment, the heating element 202a, 202b, 202c, 202d, and 202e is nickel or a nickel alloy. The temperature controller 250 thus can used the resistance of the nickel, as concluded by a resistance determining circuit. Notably, such a column 210 has a reduced mass.

As further examples, where the heating element 202a, 202b, 202c, 202d, and 202e is a column 210 for chromatographic separation, the column 210 may be constructed from a commercial fused silica column coated in nickel using an electroplating process to provide for direct heating. For indirect heating, the heating element 202a, 202b, 202c, 202d, and 202e may be a wire of nickel or containing nickel, such as a nickel-iron alloy positioned and retained in contact with the column 210. In this indirect heating, because the heating element 202a, 202b, 202c, 202d, and 202e is the entire wire, the wire heats to a consistent temperature and uniformly heats the column 210. Such construction or contact may be applied to various other components, eliminating the need for an air bath surrounding the various components, consuming valuable space and tethering the test apparatus to a fixed location.

In operation, the temperature of the component 204, 206, 208, 210, and 212 may be calculated based on resistance, may be adjusted based on signals from a temperature-measuring device such as a thermocouple, or may be controlled based on a combination of calculation and sensor readings. Such devices can be selected to further the goal of small, portable chromatographic analysis. The selection of small K-type thermocouple, for example, allows for rapid temperature. Indirect heating using nickel wire may reduce weight.

Control of the temperature of the heating element 202a, 202b, 202c, 202d, and 202e associated with the component 204, 206, 208, 210, and 212 by determination of resistance by a resistance-sensing circuit 248 and application of power, current or voltage may provide several advantages, particularly in reducing the mass of the chromatographic system 200, as components such as separate heater cartridges intermediate the heating element and the temperature controller, can be eliminated. Moreover, localized areas of increased or decreased temperature may be avoided as the heat flux is distributed over a large area, rather than emanating from a particular location associated with the heater cartridge. Further, the temperature may be more uniformly distributed as the surface area indirectly heated, or the surface area directly heated, is increased to provide an even distribution along its length rather than from one point associated with a cartridge heater.

Where the temperature of the component 204, 206, 208, 210, and 212 is to be calculated based on resistance, the temperature controller 250 may be calibrated for it. When the resistance of the heating element 202a, 202b, 202c, 202d, and 202e is not immediately known, but its normalized resistance characteristic is known, such as in the case of an unknown length or diameter of nickel wire, the temperature controller 250 may be calibrated for use with a heating element 202a, 202b, 202c, 202d, and 202e by measurement of the resistance of the heating element 202a, 202b, 202c, 202d, and 202e at one or more known temperatures from the resistance sensing circuit 248. A uniform temperature throughout a heating element 202a, 202b, 202c, 202d, and 202e may be obtained by heating the heating element 202a, 202b, 202c, 202d, and 202e in an oven. The scale factor derived by dividing the measured resistance value of the heating element 202a, 202b, 202c, 202d, and 202e by the normalized resistance value of the material from which the heating element 202a, 202b, 202c, 202d, and 202e is composed at the reference temperature may then be applied to the normalized resistance characteristic to determine the resistance of the heating element 202a, 202b, 202c, 202d, and 202e at any particular temperature.

It may be desirable that by the temperature controller 250 include a learning step to determine the responsiveness of the resistance, and therefore temperature, of the heating element 202a, 202b, 202c, 202d, and 202e to change in current, voltage or power. Determination of responsiveness is important to reduce or eliminate overshoot and/or undershoot of temperature by the temperature controller 250. Having determined the resistance of the heating element 202a, 202b, 202c, 202d, and 202e at known temperatures, the temperature controller 250 may then determine the rate of temperature increase relative to an increase in voltage, current or power by various methods known in the art, including by analyzing data pertaining to the temperature increase of the heating element 202a, 202b, 202c, 202d, and 202e in the oven per unit time compared to the temperature increase in the oven. A heating element 202a, 202b, 202c, 202d, and 202e having a large mass will exhibit a lower rate of rise of temperature proportionate to increase in current, voltage or power. Likewise, a heating element 202a, 202b, 202c, 202d, and 202e having a small mass will exhibit a high rate of rise of temperature proportionate to an increase in current, voltage or power. In each case, the change in temperature is also related to a known thermal coefficient of resistance for the material of which the heating element 202a, 202b, 202c, 202d, and 202e is composed. For the range of operation, the thermal coefficient of resistance as a function of temperature may be assumed to be known. The temperature controller 250 thereby avoids overshoot or undershoot of the desired temperature by determining in advance the responsiveness of the heating element 202a, 202b, 202c, 202d, and 202e to changes in current, voltage or power. In an alternative embodiment, the temperature controller 250 may include a look-up table of known materials used for the heating element 202a, 202b, 202c, 202d, and 202e at various temperatures and include the appropriate thermal coefficient of resistance at the temperature of the heating element 202a, 202b, 202c, 202d, and 202e to determine the associated temperature. Once the thermal coefficient of resistance of electrically-conductive material is known, the temperature of component 201a, 201b, 201c, 201d, 201e may be controlled, such that the temperature may be increased at a stepped or fixed rate to provide increased separation between compounds having similar boiling points. In a further embodiment, the temperature controller 250 may record the change in resistance as a function of the change in applied power throughout operation, thereby mapping the function throughout.

Further, the temperature controller 250 may control the heating element 202a, 202b, 202c, 202d, and 202e to provide varying temperatures to a particular device or over a corresponding period of time, such as stepped or ramped temperature increases. The heating element 202a is therefore a first electrically-controlled heating element 202a associated with the first chromatographic component 201a while the heating element 202b is a second electrically-controlled heating element 202b associated with the second chromatographic component 201b.

Where the component 204, 206, 208, 210, and 212 is comprised of electrically-conductive material such it may be directly heated, the power for producing heating is supplied through the temperature controller 250 from a power supply 258. Any number of control systems may be used to accomplish this. The current supplied to the electrically conductive material of the component 204, 206, 208, 210, and 212 may determined by the resistance-sensing circuit 248 by detecting the voltage drop across a current-sense resistor, typically 0.1 Ohms, placed between the current supply and the component 204, 206, 208, 210, and 212. Likewise, the voltage is detected. Amplifiers to properly scale the detected voltages may be used before the representative signals are passed to analog-to-digital converters. The digitized signals thereby obtained, e.g. at 1000 times per second, may be passed to a microcontroller wherein the relative resistance value is obtained by application of Ohm's Law, namely by dividing the converted voltage value by the converted current value. The relative resistance value may be compared against a reference resistance value for temperature control employing the conventional proportional-integral-derivative (PID) or another control algorithm. The temperature of the component 204, 206, 208, 210, and 212 may also be determined for display or recording by solving the equation relating temperature to resistance well known in the art or interpolating a value from a table.

Referring to FIG. 2, the illustrated chromatographic system 200 includes a temperature controller 250 in electrical communication with heating elements 202a, 202b, 202c, 202d, and 202e associated, respectively, with components 204, 206, 208, 210, and 212, namely a transfer line 204, an injection valve 206, a sample loop 208, a column 210 and a detector 212. In the illustrated embodiment, the transport line 204 is encircled by electrically conductive wiring and is therefore indirectly heated, wherein the wiring functions as the heating element 202a. In the illustrated embodiment, the injection valve 206, on the other hand, includes an internal heating element 202b for heating and is in communication with the transport line 204, with a sample loop 208 and with a column 210. In the illustrated embodiment, the sample loop 208 is in communication with the injection valve 206 and is composed of an electrically conductive material and is therefore directly heated and functions as the heating element 202c. In the illustrated embodiment, the column 210, having an electrically-conductive material positioned adjacent the body of the column 210, is indirectly heated, so that the electrically-conductive material functions as the heating element 202d. In the illustrated embodiment, the detector 212, which is in communication with the column 210, includes a heating element 202e for heating.

Referring to FIG. 2, the chromatographic system 200 further includes temperature sensors for calculation and/or signal receipt on many, though not necessarily all, components 201a, 201b, 201c, 201d, 201e. As the transport line 204 is directly heated and functions as the heating element 202a, its temperature may be controlled based on known resistance data, permitting only voltage and current to be altered to obtain the desired temperature, so the function of a temperature sensor 214a is performed by the resistance-sensing circuit 248 and the temperature controller 250. Temperature control by the temperature controller 250 of the transfer lines 204 may reduce the impact on the temperature of the column 210, particularly when a bundled (coiled with heating element 202d) column is used. Temperature control by the temperature controller 250 of the transfer lines 204 also eliminates the cold spot issue known in the prior art. Such temperature control of the transfer lines 204 may also result in higher efficiency of the rapid ramping absorb/release tube. As the injection valve 206 includes an internal heating element 202b, the valve 206 is associated with a temperature sensor 214b. The sample loop 208, indirectly heated by wiring functioning as the heating element 202c, may be accompanied by a temperature sensor 114c, such as a thermocouple and may include a current-sense resistor 116b to determine temperature based on power output. The temperature of the column 210, being indirectly heated by electrically-conductive, made be determined from its temperature sensor 214d, here a resistance sensing circuit 248. The detector 212, having a heating element 202e may also be accompanied by a temperature sensor 214e.

Referring to FIG. 2, the chromatographic system 200 may further include cooling devices, such as a fan 218, to increase heat transfer rates when cooling is desired. Such a fan 218 may be of variable speed, permitting control over the heat transfer rate associated with a particular component 201a, 201b, 201c, 201d, 201e.

The concurrent control of temperature of the various components 201a, 201b, 201c, 201d, 201e provides substantive advantages. The temperature controller 250 may provide a common temperature across the various components 201a, 201b, 201c, 201d, 201e or may be set to track the temperature of an upstream device. In a common temperature setting, the temperature controller 250 ensures each component 201a, 201b, 201c, 201d, 201e is at a common temperature setting during operation, although the temperature of each component 201a, 201b, 201c, 201d, 201e may fluctuate independently according to its own heating characteristics. In a tracking setting, the temperature controller 250 ensures each component 201a, 201b, 201c, 201d, 201e tracks the actual temperature of a monitored upstream component, ensuring the sample is maintained at the actual, though not necessarily optimum, temperature for the duration of operation.

The temperature controller thus includes a processor 252, a first electrically-controlled heating element output, a second electrically-controlled heating element output and a first temperature sensor input, a second temperature sensor input. The processor 252 is adapted to receive a first temperature sensor signal at a first temperature sensor input and to construct a first actual time-temperature profile. The processor 252 is also adapted to receive a second temperature sensor signal at a second temperature sensor input and to construct a second actual time-temperature profile. The processor 252 is adapted to receive a first time-temperature profile for the first chromatographic component 201a. The processor 252 is adapted to receive a second time-temperature profile for the second chromatographic component 201b selected from the group of the first time-temperature profile and a first actual time-temperature profile of the first chromatographic component. The processor 252 has a first power supply control for controlling a first output from the power supply 258 to the first electrically-controlled heating element output. The processor 252 has a second power supply control for controlling a second output from the power supply to the first electrically-controlled heating element output. The processor 252 is adapted to alter the first output from the power supply so the first actual time-temperature curve approaches the first actual time-temperature curve. The processor 252 is adapted to alter the second output from the power supply so the second actual time-temperature curve approaches the second time-temperature curve.

Figure 3A:
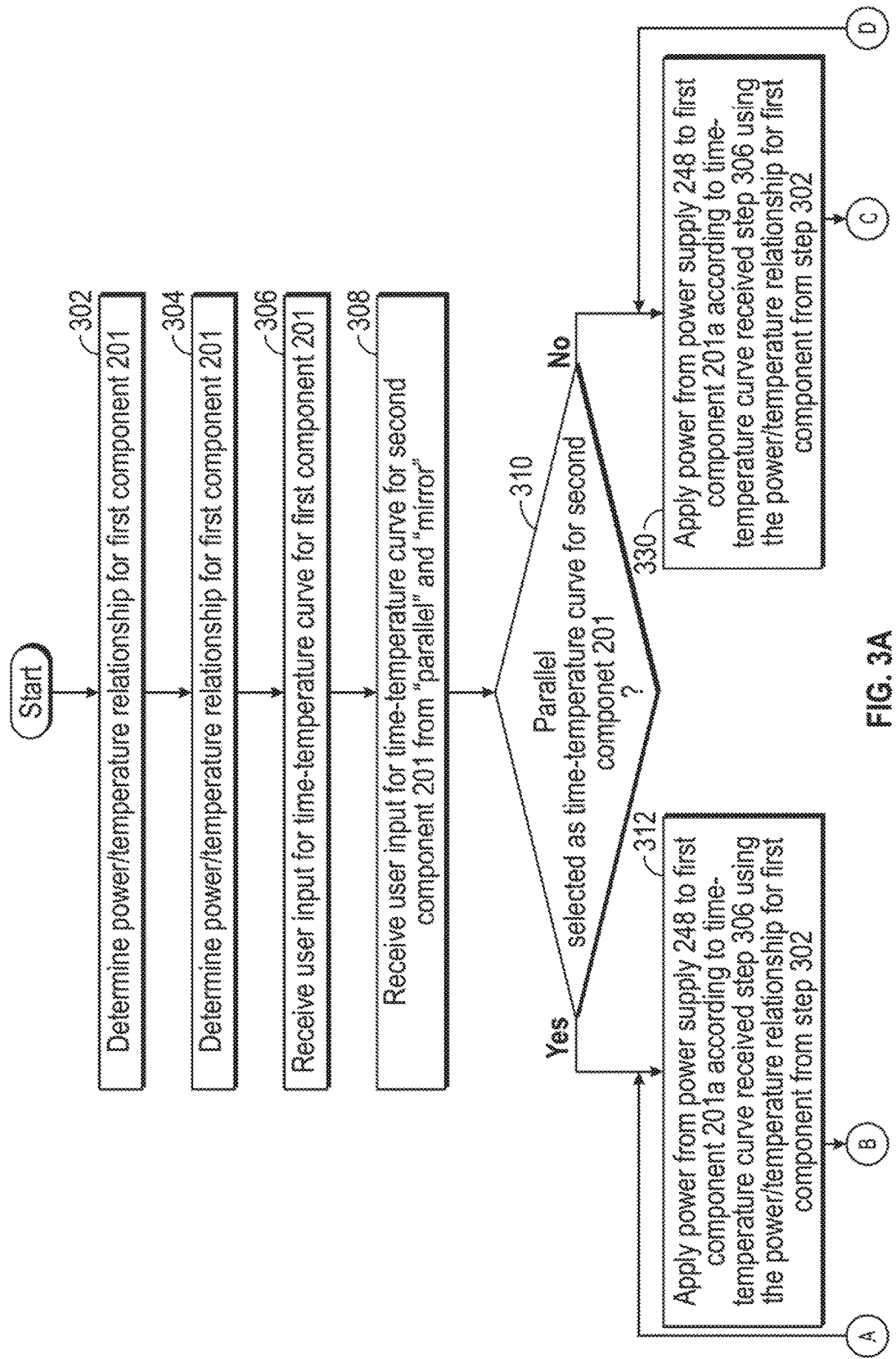
FIG. 3A illustrates the first part of one embodiment of the workflow of the present disclosure, continuing into FIGS. 3B and 3C.
Figure 3B:
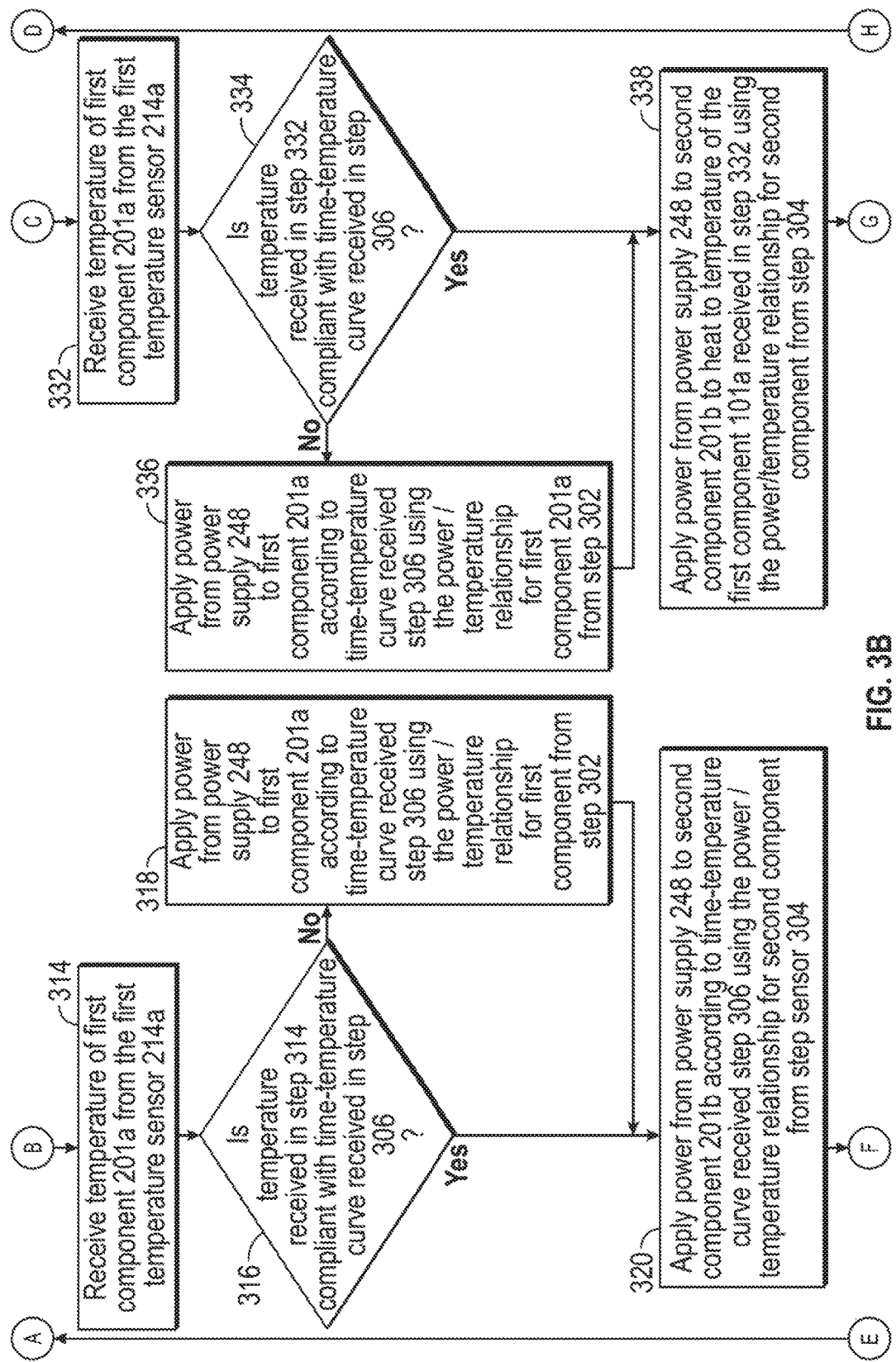
FIG. 3B illustrates the second part of one embodiment of the workflow of the present disclosure, following FIG. 3A and continuing into FIG. 3C.
Figure 3C:
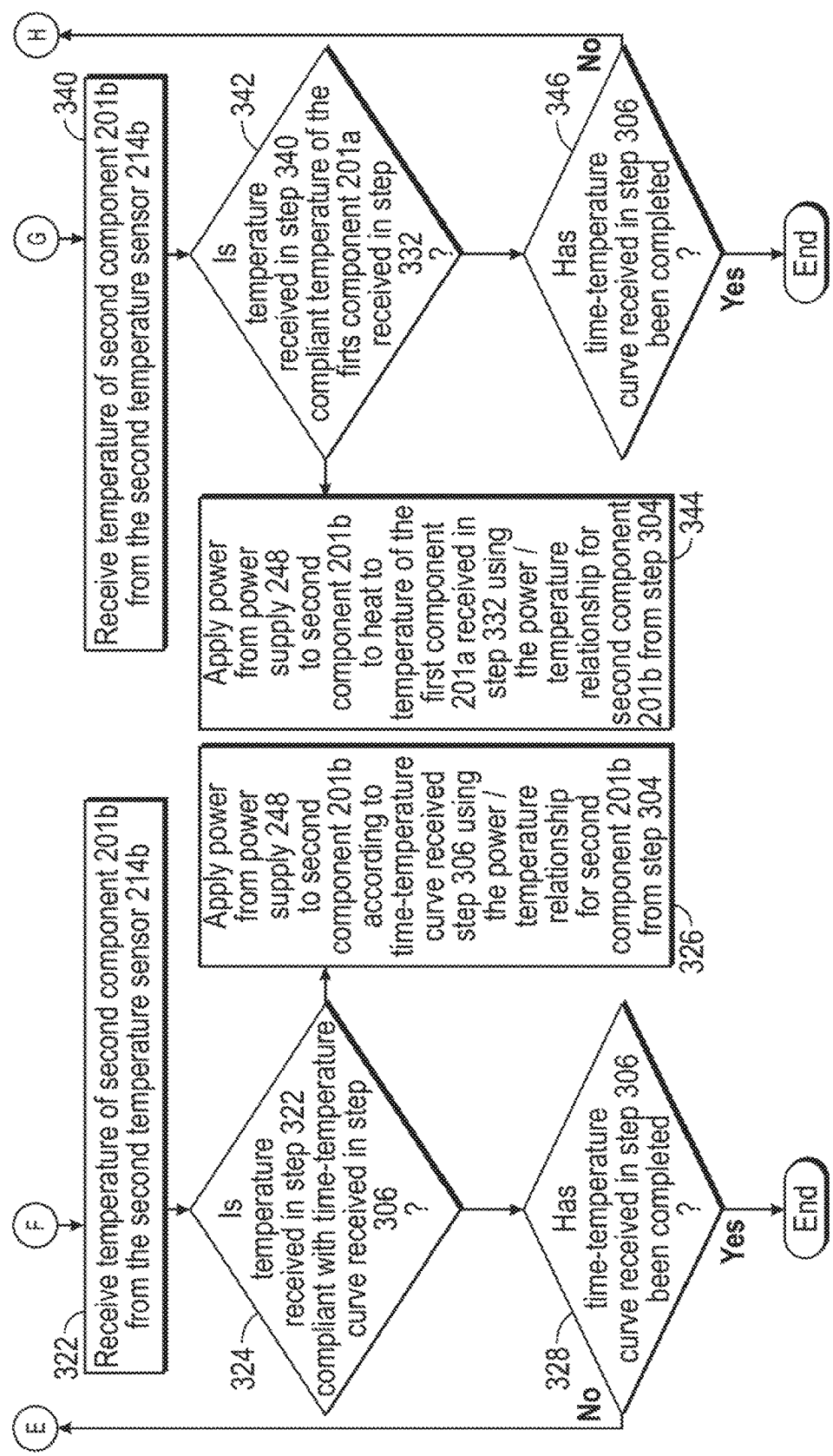
FIG. 3C illustrates the third part of one embodiment of the workflow of the present disclosure, following FIGS. 3A and 3B.

Referring to FIGS. 3A, 3B, and 3C, one embodiment of the workflow of the temperature controller 250 of the chromatographic system 200 of the present disclosure is illustrated, beginning with FIG. 3A, continuing to FIG. 3B, then FIG. 3C.

Referring to FIG. 3A, in step 302, the temperature controller 250 determines a power/temperature relationship for the first component 201a, such as the valve 206, which may be accomplishing using a temperature sensor 214b. Step 302 may be performed based on any system known in the art, such as the output from the power supply 258 and the response from the temperature sensor 214 or from the temperature sensor 214 and the resistance-sensing circuit 248, or as a function of an oven temperature and resistance-sensing circuit 248. The first chromatographic component 201a may be selected from the group comprising a transport line 204, a valve 206, a sample loop 208, a column 210, and a detector 212.

In step 304, the temperature controller 250 likewise determines a power/temperature relationship for the second component 201b, such as column 210, which may be by using a temperature sensor 114d. Step 302 may be repeated for each remaining component 201c, 201d, 201e in the chromatographic system 200. The second chromatographic component 201b may be selected from the group comprising a transport line 204, a valve 206, a sample loop 208, a column 210, and a detector 212.

In step 306, the temperature controller 250 receives a user input for a time/temperature profile for the first component 201a. This user input may be provided by a user interface 162, such as a keyboard, or from selection from a library of 164 stored time-temperature profiles.

In step 308, the temperature controller 250 receives a user input identifying whether the time/temperature profile for the second component 201b will parallel or mirror the intended time/temperature profile of the first component 201a or will track the actual time/temperature profile of the first component 201a. This user input may be provided by a user interface 162, such as a keyboard, or from selection from a library of 164 stored time-temperature profiles. Step 308 can be repeated for each remaining component 201c, 201d, 201e in the chromatographic system 200 with respect to the first component 201a.

In step 310, if the temperature controller 250 received a user input in step 308 to parallel the intended time/temperature profile of the first component 201a, the chromatograph system 200 proceeds to 312. This user input may be provided by a user interface 162, such as a keyboard, or from selection from a library of 164 stored time-temperature profiles. Otherwise the temperature controller 250 proceeds to step 330.

Parallel Operation.

In step 312, the temperature controller 250 causes the first component 201a to alter temperature, by heating or permitting cooling, pursuant to the user input from step 306, using at least one of a temperature sensor, a voltage output, and a current output for one cycle, using the power-temperature relationship determined in step 302. The temperature controller 250 may associate a first processor 252 with the first component 201a or may associate a single processor with a plurality of components 201a, 201b, 201c, 201d, 201e. Thus, the temperature controller 250 applies power from power supply 258 to first component 201a according to time-temperature curve received step 306 using the power/temperature relationship for first component 201a from step 302. The temperature controller 250 includes a first electrically-controlled heating element output wherein temperature controller 250, such as within a first processor 252, has a first power supply control for controlling the first output from the power supply 258 to the first electrically-controlled heating element output. The temperature controller 250, and particularly the first processor 252, is adapted to alter the first output from the power supply 258 so a first actual time-temperature curve approaches the first time-temperature curve of step 308.

Referring to FIG. 3B, in step 314, the temperature controller 250 takes a temperature measurement of the first component 201a. As provided previously, this temperature measurement may be by a resistance measurement or a temperature sensor 214a, such as a thermocouple, and provided to the temperature controller 250 and/or to the first processor 252. Thus, the temperature controller 250 receives the temperature of first component 201a from the first temperature sensor 214a.

In step 316, the temperature controller 250 compares the temperature measurement of step 314 to the time/temperature profile for the first component 201a received in step 306. This comparison may be performed in the first processor 252. The temperature controller 250 thus determines whether the temperature received in step 314 is compliant with the time-temperature curve received in step 306. If the temperature measurement of step 316 matches the time/temperature profile for the first component 201a received in step 306, the temperature controller 250 proceeds to step 320. Otherwise the temperature controller 250 proceeds to step 318.

In step 318, the temperature controller 250 adjusts the power output from a power supply 258 to the first component 201a to match the time/temperature profile for the first component 201a received in step 306. Where necessary, a fan 218 or other cooling device, is associated with the temperature controller with the heat transfer rate is insufficient to adequately reduce the temperature of the first component 201a. Preferably, the temperature of the first component 201a is maintained within 0.1° C. for isothermal, within 1.0° C. for temperature programming, or 10% of the intended temperature from the actual temperature identified in the previous cycle. This adjustment may be controlled by the first processor 252. The temperature controller 250 than proceeds to step 320. The temperature controller 250 applies power from power supply 258 to the first component 201a according to time-temperature curve received in step 306 using the power/temperature relationship for the first component 201a from step 302.

In step 320, the temperature controller 250 causes the second component 201b to alter temperature, by heating or permitting cooling, pursuant to the user input from step 306, using at least one of a temperature sensor, a voltage output, and a current output for one cycle, using the power-temperature relationship determined in step 304, mirroring the time/temperature profile for the first component 201a. The temperature controller 250 therefore applies power from the power supply 258 to the second component 201b according to time-temperature curve received in step 306 using the power/temperature relationship for the second component 201b from step 304. The temperature controller 250 may associate a second processor 254 with the second component 201a. The temperature controller 250 includes a second electrically-controlled heating element output wherein the temperature controller 250, such as within a first processor 252 or a second processor 254, has a second power supply control for controlling the second output from the power supply 258 to the second electrically-controlled heating element output. The temperature controller 250, and particularly the first processor 252 or second processor 254, is adapted to alter the second output from the power supply 258 so a second actual time-temperature curve approaches the first time-temperature curve of step 308.

Referring to FIG. 3C, in step 322, the temperature controller 250 takes a temperature measurement of the second component 201b. As provided previously, this temperature measurement may be by a resistance measurement or a temperature sensor 214b, such as a thermocouple, and provided to the temperature controller 250 and/or to the second processor 254. The temperature controller 250 receives the temperature of second component 201b from the second temperature sensor 214b.

In step 324, the temperature controller 250 compares the temperature measurement of step 322 to the time/temperature profile for the first component 201a received in step 306. This comparison may be performed in the second processor 254. If the temperature measurement of step 322 matches the time/temperature profile for the first component 201a received in step 306, the temperature controller 250 proceeds to step 330. Otherwise the temperature controller 250 proceeds to step 326.

In step 326, the temperature controller 250 adjusts the power output from a power supply 258 or a second power supply 160 to the second component 201b to match the time/temperature profile for the first component 201a received in step 306. The temperature controller 250 applies power from the power supply 258 to the second component 201b according to time-temperature curve received in step 306 using the power/temperature relationship for the second component 201b from step 304. Where necessary, a fan 218 or other cooling device, is associated with the temperature controller with the heat transfer rate is insufficient to adequately reduce the temperature of the second component 201b. Preferably, the temperature of the second component 201b is maintained within 10% of the intended temperature from the actual temperature identified in the previous cycle. This adjustment may be controlled by the first processor 252. The temperature controller than proceeds to step 328. As can be appreciated, the temperature control 250 performs steps identical to those of steps 320-326 if additional components 201c, 201d, 201e are included for each of those components 201c, 201d, 201e before proceeding to step 328. Each additional component 201c, 201d, 201e may likewise have a separate processor associated with it.

In step 328, the temperature controller 250 determines whether the time of the time/temperature profile for the first component 201a received in step 306 has elapsed or been completed. If the duration has not elapsed or been completed, the temperature controller 250 returns to step 312. If the duration has elapsed, the temperature controller 250 terminates operation.

Tracking Operation

In step 330, the temperature controller 250 causes the first component 201a to alter temperature, by heating or permitting cooling, pursuant to the user input from step 306, using at least one of a temperature sensor, a voltage output, and a current output for one cycle, using the power-temperature relationship determined in step 302. The temperature controller 250 applies power from the power supply 258 to the first component 201a according to time-temperature curve received step 306 using the power/temperature relationship for the first component from step 302. The temperature controller 250 may associate a first processor 252 with the first component 201a or may associate a single processor with a plurality of components 201a, 201b, 201c, 201d, 201e. The temperature controller 250 includes a first electrically-controlled heating element output wherein temperature controller 250, such as within a first processor 252, has a first power supply control for controlling the first output from the power supply 258 to the first electrically-controlled heating element output. The temperature controller 250, and particularly the first processor 252, is adapted to alter the first output from the power supply 258 so a first actual time-temperature curve approaches the first time-temperature curve of step 308.

Referring to FIG. 3B, in step 332, the temperature controller 250 takes a temperature measurement of the first component 201a. The temperature controller 250 receives temperature of the first component 201a from the first temperature sensor 214a. As provided previously, this temperature measurement may be by a resistance measurement or a temperature sensor 214a, such as a thermocouple, and provided to the temperature controller 250 and/or to the first processor 252. The temperature measurement of the first component 201a may be provided as a signal and may also be provided to the second processor 254.

In step 334, the temperature controller 250 compares the temperature measurement of step 332 to the time/temperature profile for the first component 201a received in step 306. The temperature sensor 250 assesses whether the temperature received in step 332 is compliant with the time-temperature curve received in step 306. This comparison may be performed in the first processor 252. If the temperature measurement of step 332 matches the time/temperature profile for the first component 201a received in step 306, the temperature controller 250 proceeds to step 338. Otherwise the temperature controller proceeds to step 336. Compiling the temperature measurements of step 332 provides an actual time-temperature profile of the first component 201a.

In step 336, the temperature controller 250 adjusts the power output from a power supply 258 to the first component 201a to match the time/temperature profile for the first component 201a received in step 306. The temperature controller 250 applies power from the power supply 258 to the first component 201a according to time-temperature curve received in step 306 using the power/temperature relationship for the first component 201a from step 302. Where necessary, a fan 218 or other cooling device, is associated with the temperature controller with the heat transfer rate is insufficient to adequately reduce the temperature of the first component 201a. Preferably, the temperature of the first component 201a is maintained within 10% of the intended temperature from the actual temperature identified in the previous cycle. The temperature controller than proceeds to step 338.

In step 338, the temperature controller 250 causes the second component 201b to alter temperature, by heating or permitting cooling, to match the actual temperature profile for the first component 201a received in step 332, using at least one of a temperature sensor, a voltage output, and a current output for one cycle, using the power-temperature relationship determined in step 304, paralleling the actual time/temperature profile for the first component 201a. The temperature controller 250 applies power from power supply 258 to the second component 201b to alter temperature, by heating or permitting cooling, to the temperature of the first component 201a received in step 332 using the power/temperature relationship for second component 201b from step 304. The temperature measurement of the first component 201a may have been obtained as a signal from the first processor 252. The temperature of the second component 201b is thus targeted to match, for the appropriate cycle, the actual temperature of the first component 201a. The temperature controller 250 includes a second electrically-controlled heating element output wherein the temperature controller 250, such as within a first processor 252 or a second processor 254, has a second power supply control for controlling the second output from the power supply 258 to the second electrically-controlled heating element output. The temperature controller 250, and particularly the first processor 252 or second processor 254, is adapted to alter the second output from the power supply 258 so a second actual time-temperature curve approaches the first actual time-temperature curve of step 332.

Referring to FIG. 3C, in step 340, the temperature controller 250 takes a temperature measurement of the second component 201b. The temperature controller 250 receives the temperature of the second component 201b from the second temperature sensor 214b. As provided previously, this temperature measurement may be by a resistance measurement or a temperature sensor 214b, such as a thermocouple, and provided to the temperature controller 250 and/or to the second processor 254.

In step 342, the temperature controller 250 compares the temperature measurement of step 324 to actual temperature for the first component 201a received in step 332. The temperature controller 250 assesses whether the temperature received in step 340 is compliant with the temperature of the first component 201a received in step 332. This comparison may be performed in the second processor 254. If the temperature measurement of step 340 matches the actual temperature profile for the first component 201a received in step 332, the temperature controller 250 proceeds to step 330. Otherwise the temperature controller proceeds to step 346.

In step 344, the temperature controller 250 adjusts the power output to the second component 201b from a power supply 258 or a second power supply 160 to match the temperature profile for the first component 201a received in step 332. The temperature controller 250 applies power from the power supply 258 to the second component 201b to alter the temperature of the second component 201b to match the first component 201a received in step 332 using the power/temperature relationship for second component 201b from step 304. Where necessary, a fan 218 or other cooling device, is associated with the temperature controller when the heat transfer rate of the component 201a, 201b, 201c, 201d, 201e is insufficient to adequately reduce the temperature of the second component 201b. Preferably, the temperature of the second component 201b is maintained within 10% of the intended temperature from the actual temperature identified in the previous cycle. The temperature controller than proceeds to step 346. Preferably, the temperature of the second component 201*b* is maintained within 10% of the intended temperature from the actual temperature identified in the previous cycle. As can be appreciated, the temperature control 250 performs steps identical to those of steps 338-344 if additional components 201*c*, 201*d*, 201*e* are included for each of those components 201*c*, 201*d*, 201*e* before proceeding to step 328.

In step 346, the temperature controller 250 determines whether the time of the time/temperature profile for the first component 201*a* received in step 306 has elapsed or been completed. If the duration has not elapsed or been completed, the temperature controller 250 returns to step 330. If the duration has elapsed, the temperature controller 250 terminates operation.

Other temperature regimes are likewise possible. Each component 201*a*, 201*b*, 201*c*, 201*d*, 201*e*, for example, may have a unique time-temperature profile, effectively independently processing according to steps 302, 306, 312-318 and 328. Because each component 201*a*, 201*b*, 201*c*, 201*d*, 201*e* may have its own time-temperature profile, each component 201*a*, 201*b*, 201*c*, 201*d*, 201*e*, or groups of components 201*a*, 201*b*, 201*c*, 201*d*, 201*e* in a zone, can be associated with a different temperature sensor 214*a*, 214*b*, 214*c*, 214*d*, 214*e*, and can be programmed to start and stop temperature ramping, according to a profile, simultaneously or independently. The first temperature sensor 214*a* is thus associated with the first chromatographic component 201*a* while the second temperature sensor 214*b* is associated with the second chromatographic component 201*b*. The first temperature sensor 214*a* generates a first temperature sensor signal, while the second temperature sensor 214*b* generating a second temperature sensor signal.

Thus, in operation, the temperature controller 250 of the present disclosure simultaneously controls a plurality of components 201*a*, 201*b*, 201*c*, 201*d*, 201*e* with components set to mirror or track the intended or actual temperature profile of another component 201*a*, 201*b*, 201*c*, 201*d*, 201*e* in a rapid and controlled fashion. Beneficially, the temperature controller 250 provides fast ramping temperatures and cooling, particularly when associated with heating elements 202*a*, 202*b*, 202*c*, 202*d*, 202*e* made of electrically-conductive material and integrated into the body of the component 201*a*, 201*b*, 201*c*, 201*d*, 201*e*, particularly where the body of the component 201*a*, 201*b*, 201*c*, 201*d*, 201*e* is, itself, composed in part or jacketed by the electrically-conductive material. Regardless, because of the separate control over separate components 201*a*, 201*b*, 201*c*, 201*d*, 201*e* and elimination of unnecessary heating of the surrounding volume of air, temperature controller 250 permits a smaller size and a reduced power consumption compared to the prior art.

The temperature controller 250, in connection with the simultaneously and commonly controlled components 201*a*, 201*b*, 201*c*, 201*d*, 201*e* or zones can more rapidly perform chromatographic analysis, may permit use of a column 210 of smaller size, may produce a system of higher sensitivity, and, because heating is localized to the components 201*a*, 201*b*, 201*c*, 201*d*, 201*e*, may consume less power.

The terms and expressions which have been employed in the foregoing specification are used therein as terms of description and not of limitation, and there is no intention, in the use of such terms and expressions, of excluding equivalents of the features shown and described or portions thereof.

We claim:

1. A method for controlling at least two chromatographic components in a chromatographic system, comprising:
   determining a power/temperature relationship for a first component;
   determining a power/temperature relationship for a second component;
   receiving a time/temperature profile for the first component;
   receiving an input identifying whether a time/temperature profile for the second component will track an actual time/temperature profile of the first component;
   applying power to the first component to alter a temperature of the first component according to the power-temperature relationship for the first component;
   obtaining a temperature measurement of the first component;
   constructing the actual time-temperature profile of the first component;
   adjusting a first component power supplied to the first component to alter the temperature of the first component according to the power-temperature relationship for the first component as determined by the temperature measurement of the first component;
   applying a second component power to the second component to alter the temperature of the second component according to one of the power-temperature relationship for the first component and the actual time-temperature profile of the first component;
   obtaining a temperature measurement of the second component;
   adjusting the first component power supplied to the first component to alter the temperature of the second component according to one of the group of relationships consisting of the power-temperature relationship for the first component and the actual time-temperature profile of the first component as determined by the temperature measurement of the second component.

* * * * *